Feb. 18, 1958 E. S. BOERNER Plant Pat. 1,683
ROSE PLANT
Filed July 5, 1957
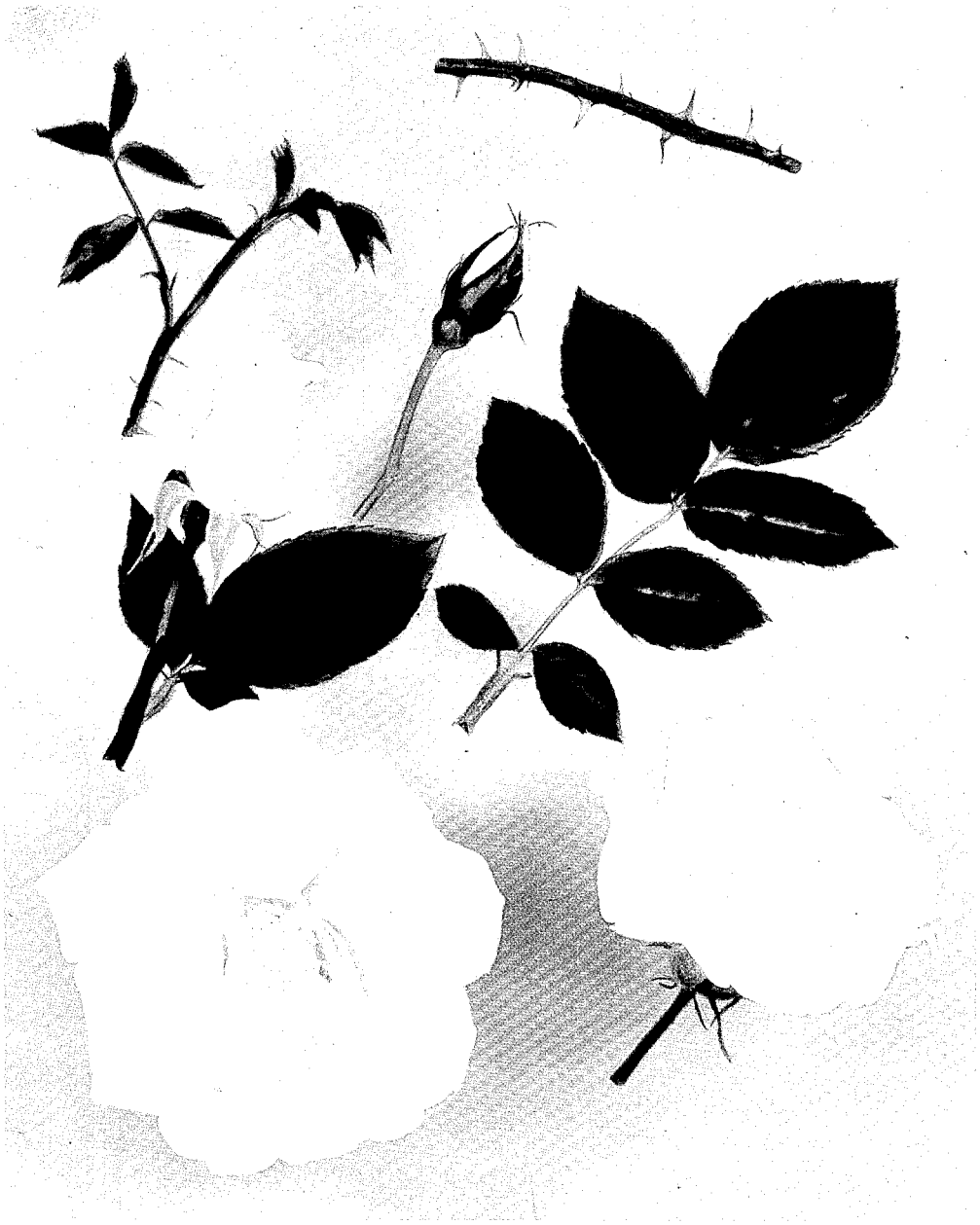
Inventor.
E. S. Boerner
By: Robb & Robb
Attorneys.

United States Patent Office

Plant Pat. 1,683
Patented Feb. 18, 1958

1,683

ROSE PLANT

Eugene S. Boerner, Newark, N. Y., assignor to Jackson & Perkins Company, Newark, N. Y., a corporation of New York Application July 5, 1957, Serial No. 670,352

1 Claim. (Cl. 47—61)

The present invention relates to a new and distinct variety of rose plant of the large-flowered polyantha class, which was originated by me by crossing an unnamed and unpatented yellow floribunda seedling of "Goldilocks" (Plant Patent No. 672) × an unnamed and unpatented hybrid tea variety, with an unnamed and unpatented yellow floribunda seedling of "King Midas" Climber (Plant Patent No. 586) × an unnamed and unpatented hybrid tea seedling.

The primary objective of this breeding was to produce a new floribunda rose which has glossy foliage and rich-colored flowers. This objective was fully achieved, along with other improved features which, when considered altogether, represent a new combination in a floribunda rose and distinguished the new variety from its parents, as well as from all other varieties of its class of which I am aware.

The new variety is particularly characterized as to novelty by the following outstanding features:

(1) Its vigorous growth;

(2) Its glossy foliage;

(3) The Empire Yellow general color tonality of its flowers, and the unfading quality thereof to the end of the blooms; and (4) The unusual and very strong fragrance of its flowers.

Asexual reproduction of the new variety by budding, as performed at Newark, New York, and also at Pleasanton, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—An unnamed yellow floribunda seedling of "Goldilocks" × an unnamed hybrid tea seedling.

*Pollen parent.*—An unnamed yellow floribunda seedling of "King Midas" × an unnamed hybrid tea seedling.

Classification:

*Botanic.*—Large-flowered polyantha.

*Commercial.*—Floribunda.

*Flower*

(Observations made from specimens grown outdoors at Newark, New York, near mid-morning and in the middle of the month of October.)

Blooming habit: Recurrent—continuous.

Bud:

*Size.*—Large.

*Form.*—Ovoid pointed; is not affected by wet or hot weather.

*Color.*—When sepals first divide—Carmine, Plate 1. When petals begin to unfurl—Empire Yellow, Plate 4. When half-blown: inside of petals—Empire Yellow, Plate 4, with lower half of petal lightly overcast with Light Cadmium, Plate 4; reverse of petals—Pale Lemon Yellow, Plate 4, lightly overcast with Empire Yellow, Plate 4.

*Sepals.*—Slightly branched; curled back when petals begin to unfurl. Color: inside—Light Dull Green-Yellow, Plate 17; outside—Chromium Green, Plate 32.

*Calyx.*—Color—Biscay Green, Plate 17. Shape—pear. Size—small. Aspect—smooth. Odor when rubbed—none.

*Peduncle.*—Length—medium. Aspect—smooth. Strength—erect; slender. Color—Lettuce Green, Plate 5.

*Opening.*—Opens up well; is not affected by adverse weather conditions.

Bloom:

*Size.*—Large. Average size when fully expanded—4½ inches.

*Borne.*—Several together and in flat clusters.

*Stems.*—Medium length; strong.

*Form (when first open).*—Open. Permanence—retains its form to the end, but outer petals curl back.

*Petalage.*—Semi-double. Number of petals under normal conditions—from 25 to 30.

*Color.*—Center of flower—Empire Yellow, Plate 4. Outer petals—Pinard Yellow, Plate 4, with lower half of petal lightly overcast with Empire Yellow, Plate 4. Base of petals (aiglet)—Lemon Chrome, Plate 4. Inside of petals—Empire Yellow, Plate 4, with outer edge of petal lightly overcast with Pinard Yellow, Plate 4. Reverse of petals—Pinard Yellow, Plate 4, with lower half of petal lightly overcast with Martius Yellow, Plate 4. General tonality from a distance—Empire Yellow, Plate 4.

*Discoloration.*—General tonality at end of first day—Empire Yellow, Plate 4. Second day—Pinard Yellow, Plate 4. Third day—Pinard Yellow, Plate 4, lightly overcast with Martius Yellow, Plate 4.

Petals:

*Texture.*—Leathery; is not affected by wet or hot weather.

*Appearance.*—Inside—satiny. Outside—shiny.

*Form.*—Oval; slightly notched.

*Arrangement.*—Imbricated (regularly arranged shingle-like).

*Petaloids in center.*—Few; large.

*Persistence.*—Drop off cleanly.

*Fragrance.*—Very strong. Nature—"Old Rose perfume" (centifolia).

*Lasting quality.*—On the plant—long. As cut flower—long.

*Genital organs*

Stamens, anthers: Medium size; many; regularly arranged around styles. Color—Light Cadmium, Plate 4.

Stamens, filaments (threads): Long. Color—Empire Yellow, Plate 4.

Pollen: Color—Baryta Yellow, Plate 4.

Styles: Columnar; uneven length; long; thin.

Stigmas: Color—Pale Lemon Yellow, Plate 4.

Ovaries: All enclosed in calyx.

Hips: None.

Seeds: None.

*Plant*

Form: Bush.
Growth: Very vigorous; upright.
Foliage: Compound of 5 to 7 leaflets or more.
*Size.*—Medium.
*Quantity.*—Abundant.
*Color.*—New foliage: upper side—Parrot Green, Plate 6, with edges overcast with Oxblood Red, Plate 1; under side—Cosse Green, Plate 5, lightly overcast with Oxblood Red, Plate 1. Old foliage: upper side—Varley's Green, Plate 18; under side—Biscay Green, Plate 17.
*Shape.*—Oval pointed.
*Texture.*—Upper side—leathery; glossy. Under side—smooth.
*Ribs and veins.*—Ordinary.
*Edge.*—Serrated (saw-toothed).
*Serration.*—Both double and single; small.
*Leaf stem.*—Color—Courge Green, Plate 17. Under side—Prickly.
*Stipules.*—Long; smooth.
Wood:
*New wood.*—Color—Oil Green, Plate 5. Bark—smooth.

*Old wood.*—Color—Light Elm Green, Plate 17. Bark—smooth.
Thorns:
*Thorns.*—Quantity: on main stalks from base—ordinary; on laterals from stalk—many. Form—flat base; medium length; straight. Color (when young)—Rose Doree, Plate 1. Position—irregular.
*Prickles.*—Quantity: on main stalks—none; on laterals—none.
*Short needles.*—Quantity: on main stalks—none; on laterals—none.

I claim:

A new and distinct variety of rose plant of the large-flowered polyantha class, substantially as herein shown and described, characterized particularly as to novelty by its vigorous growth, glossy foliage, the rich Empire Yellow general color tonality of its flowers, and their good color retention to the end of the blooms, and the unusual and very strong fragrance of its flowers.

No references cited.